(12) United States Patent
Gerstel

(10) Patent No.: US 8,925,369 B2
(45) Date of Patent: Jan. 6, 2015

(54) DEVICE AND METHOD FOR PREPARING SAMPLES FOR GAS CHROMATOGRAPHY

(75) Inventor: Joachim Gerstel, Mülheim an der Ruhr (DE)

(73) Assignee: Joint Analytical Systems GmbH, Moers (DE)

(*) Notice: Subject to any disclaimer, the term of this patent is extended or adjusted under 35 U.S.C. 154(b) by 600 days.

(21) Appl. No.: 13/198,616

(22) Filed: Aug. 4, 2011

(65) Prior Publication Data

US 2011/0283771 A1    Nov. 24, 2011

Related U.S. Application Data

(63) Continuation-in-part of application No. PCT/EP2010/051064, filed on Jan. 29, 2010.

(30) Foreign Application Priority Data

Feb. 4, 2009    (DE) .......................... 10 2009 003 429

(51) Int. Cl.
*G01N 1/00* (2006.01)
*G01N 30/10* (2006.01)
*G01N 30/12* (2006.01)

(52) U.S. Cl.
CPC .......... *G01N 30/10* (2013.01); *G01N 2030/126* (2013.01); *G01N 30/12* (2013.01)
USPC ...................................................... 73/23.41

(58) Field of Classification Search
USPC ...................................................... 73/23.41
See application file for complete search history.

(56) References Cited

U.S. PATENT DOCUMENTS 5,686,656 A * 11/1997 Amirav et al. ............... 73/23.41
6,180,410 B1    1/2001 Gerstel et al.

(Continued)

FOREIGN PATENT DOCUMENTS

CN    1268667    10/2000
CN    1721850    1/2006

(Continued)

OTHER PUBLICATIONS

Yang Zhiyan, et al.; "A Multi-Step Distillation Method for Sample Preparation in Gas Chromatographic Analysis"; Chinese Journal of Chromatography; vol. 25, No. 5; pp. 654-656, Sep. 2007.

*Primary Examiner* — Hezron E Williams
*Assistant Examiner* — Rodney T Frank
(74) *Attorney, Agent, or Firm* — Thorpe North & Western LLP

(57) ABSTRACT

An apparatus (10) for preparing samples (62) for gas chromatography contains a tubular liner (16) which can be flooded with carrier gas (64) and has a lower end region which can be heated in a controlled manner; a sample reservoir (26) which can be heated in a controlled manner; an active material (20) provided in the lower end region of the liner (16); an outer tube (38) which is arranged coaxially around the liner, wherein a cavity (46) which is connected to the lower end region of the liner is formed between the liner and the outer tube; a splitter exit (48) on the outer tube (38); a carrier gas connection (52) which is provided on the outer tube (38) and is intended to supply carrier gas (82) to the cavity (46); a column connection (22) which is provided above the active material (20) and is intended to connect a gas chromatography column (12); and control means for controlling the carrier gas stream, in a first setting (FIG. 1), from the interior (24) of the liner (16) through the active material (20) into the cavity (46) and from there to the splitter exit (48) and, in a second setting (FIG. 2), from the carrier gas connection (52) in the opposite direction through the cavity (46) and through the active material (20) to the column connection (22).

13 Claims, 2 Drawing Sheets

(56) References Cited

U.S. PATENT DOCUMENTS

| | | |
|---|---|---|
| 6,779,379 B2 | 8/2004 | Grob et al. |
| 2006/0245975 A1 | 11/2006 | Tipler et al. |
| 2008/0098887 A1* | 5/2008 | Tipler et al. ................ 95/22 |

FOREIGN PATENT DOCUMENTS

| | | |
|---|---|---|
| JP | 02-089356 | 7/1990 |
| JP | H 05-157742 | 6/1993 |
| JP | 06-082434 | 3/1994 |
| JP | H 07-31801 | 2/1995 |
| JP | 08-297115 | 11/1996 |
| JP | 09-033502 | 2/1997 |
| JP | 09-159660 | 6/1997 |
| JP | 11-218527 | 8/1999 |
| JP | 11-337541 | 12/1999 |
| JP | 2000/155113 | 6/2000 |
| JP | 2002/174629 | 6/2002 |
| JP | 2006/516717 | 7/2006 |
| JP | 2008/256714 | 10/2008 |
| JP | 2009/092672 | 4/2009 |
| WO | WO 94/28409 | 12/1994 |
| WO | WO 2006/077912 | 7/2006 |

* cited by examiner

DEVICE AND METHOD FOR PREPARING SAMPLES FOR GAS CHROMATOGRAPHY

RELATED APPLICATIONS

This application is a continuation-in-part of International Application PCT/EP2010/051064 filed Jan. 29, 2010, and which specified the United States, and which is based on and claims priority to German Application DE 10 2009 003 429.3 filed Feb. 4, 2009.

TECHNICAL FIELD

The invention relates to a device for the preparation of samples for gas chromatography, comprising:
(a) a tubular liner adapted to be flushed with carrier gas;
(b) a controllably heated sample reservoir;
(c) an active material provided in the liner;
(d) an outer tube coaxially arranged around the liner, wherein a space is formed between the liner and the outer tube, the space being in contact with the lower end portion of the liner;
(e) a split outlet at the outer tube;
(f) a carrier gas connection provided at the outer tube for feeding carrier gas into the space;
(g) a column connection above the active material for connecting a gas chromatographic column; and
(h) control means for controlling the carrier gas flow
 in a first setting from the inside of the liner through the active material, and
 in a second setting from the carrier gas connection in the opposite direction through the active material to the column connection.

The invention also relates to a method for the preparation of samples for analytic purposes, comprising the steps of:
(a) generating a gas flow comprising a gaseous sample by evaporation of a sample and generating a carrier gas flow containing the sample vapour;
(b) flowing the carrier gas flow comprising the sample vapour through an active material comprised in a container placed in an outer tube, the active material selected in such a way that the sample remains in the active material and the remaining gas flow passes through the active material;
(c) removing the carrier gas flow passed through the active material through a space formed between the container and the outer tube and through a split outlet towards the outside;
(d) generating a carrier gas flow through the active material in the opposite direction in order to include the sample contained in the active material into the carrier gas flow; and
(e) flowing the sample-carrier gas flow to a gas chromatography column.

It is known to insert samples into gas chromatographic columns by means of a sampling device. Such sampling devices comprise a sampling head, a tubular sampling chamber connected to the sampling head and adapted to be heated by an electric heating according to a program, a liner inside the sampling chamber, adapted to receive the end of a gas chromatographic separating column at its end remote to the end of the sampling head and means for introducing carrier gas into the liner.

Such sampling chambers are, for example, known from an article by Schomburg "Probenaufgabe in der Kapillargaschromatographie" in the DE Journal "LABO Kennziffer Fachzeitschrift für Labortechnik" Edition July 1983, pages 37 to 46 and from DE 34 48 091 C3.

For sampling a liquid sample into a gaschromatograph normally the sample is dissolved in a solvent for obtaining amounts which are easy to handle. The dissolved sample is injected with an injection needle through a sampling head with a septum or a heated valve into the carrier gas flow. The carrier gas flow carries the sample and the solvent through a liner. The liner, which normally consists of glass, sits in a sampling chamber heated by a heating. In the publication in LABO this heating is an air heating, where the air is heated by a heating coil. In DE 34 48 091 C3 the sampling chamber is a tube surrounded by a heating coil. The liner sits in the middle of the tube shaped sampling chamber. An annular space is formed between the liner and the sampling chamber. The sampling chamber and thereby the liner are adapted to be heated according to a program.

In "split"-operation at first the highly volatile solvent is evaporated. This evaporated solvent flows through the liner and the annular space and is removed through the split outlet. Subsequently, the sample itself is evaporated by a "ballistic" heating to higher temperatures. A separating column, preferably a capillary column requiring and processing only small amounts of sample, extends into the end of the liner opposite to the inlet with its inlet end. The sample is carried by the carrier gas into the separating column. The separating column is heated according to a temperature program.

As a larger volume of sample gas is generated in the liner a focusing of the sample is effected at the inlet of the separating column. The temperature of the separating column is maintained low at first. This causes a small carrier velocity of all components of the sample in the separating column. A plug of sample gas is formed at the inlet of the separating column. Upon increasing temperature in the separating column the differences of volatility of the various sample components become more apparent and cause different carrier velocities and thereby a resolution of the sample in peaks which separately appear at the outlet of the separating column.

Known sampling heads require difficult sample preparation for removal of a possibly interfering matrix.

In the publication "Monitoring industrial wastewater by online GC-MS with direct aqueous injection" by M. Wortberg, W. Ziemer, M. Kugel, H. Müller and H.-J. Neu in Anal. Bioanal. Chem (2006) 384; 1113-1122 an assembly is described where a closed injector is used without a split outlet. The sample is evaporated in the evaporation volume of the injector. The evaporated sample is fed to a liner outside the evaporation volume afterwards. The liner is filled with Tenax TA. The sample will remain in the cold liner while water steam is removed. Subsequently, the liner is heated and the sample is inserted into the column.

WO2005/04786A2 discloses an assembly for pre-concentrating samples for gas chromatography. The sample is flowed through an adsorbent. Afterwards, the sample is backflushed from the adsorbent in the opposite direction.

U.S. Pat. No. 6,402,947 describes an adapter for automated transfer of a sample from a liquid chromatography column into a gas chromatography column for both, reverse phase and for normal phase chromatography. The assembly is provided with a liner having three connections: the end of a liquid chromatography column, the entrance of a gas chromatography column and a connection for removing solvent. Carrier gas flows into the liner in a transfer mode and through an adsorbent present in the liner. The sample is inserted from the liquid chromatography column into the liner in the transfer mode. The sample is adsorbed by an adsorbent in an adsorption mode and in a desorption mode the adsorbent is flushed by carrier gas in the opposite direction while including the sample and carrying it to the gas chromatography column.

The assembly requires many valves, pressure regulators and connections. It is, therefore, complex and expensive to manufacture.

DISCLOSURE OF THE INVENTION

It is an object of the invention to provide a device and a method of the aforementioned kind, which facilitates the sample preparation and increases the accuracy of the analytic results.

According to the invention, this object is achieved by a device for the preparation of samples for gas chromatography, which is characterized in that (i) the lower end portion of the liner is adapted to be controllably heated;
(j) the sample reservoir is placed inside the liner or is adapted to be inserted into the liner together with the sample;
(k) the active material is provided in the controllably heated, lower end portion of the liner;
(l) the column connection for connecting a gas chromatographic column is provided above the active material;
(m) the carrier gas flow is flowed in the first setting from the active material into the space and from there to the split outlet; and
(n) the carrier gas flow in the second setting flows in the opposite direction through the space and afterwards through the active material.

With such a device the sample can be inserted into the liner together with the sample reservoir. Alternatively, the sample is introduced into a sample reservoir which is already present in the liner. The sample reservoir may be present in the upper end portion of the liner. In particular, the sample reservoir can be magnetically mounted in the upper end portion of the liner.

In a further, alternative embodiment, the sample reservoir is positioned outside the liner. This is particularly useful if large amounts of sample are available. With this embodiment the sample reservoir can be activated by means of an autosampler.

The device enables a slow evaporation of the sample together with the solvent independently of the temperature of the liner and independent of further sample preparation steps.

The evaporated sample enters the liner together with the solvent in a first step. The liner is then flushed with carrier gas. The carrier gas can be introduced in this step through a connection at the liner or in the plug of the liner. The sample is passed through the active material together with the carrier gas and remains there. The active material may be an adsorbent or a phase material. The active material can be placed in the liner on a glass frit a porous glass bottom of the liner or the like. The carrier gas leaves through the glass frit or the glass bottom at the lower end of the liner. From there, it passes through the space between the liner and the outer tube. The carrier gas is removed through the split outlet.

If the sample is completely evaporated and is present in the range of the active material, the carrier gas flow is reversed in a second method step. The carrier gas will then enter the space between the liner and the outer tube through the carrier gas connection at the outer tube. Simultaneously, the column connection, which was previously closed, is opened. The carrier gas now flows in the opposite direction through the space and through the active material. There it carries the sample with it. Afterwards, it is fed to the column through the column connection.

Preferably, the active material can be heated and/or cooled. With cooling the retaining of the evaporated sample in the first step is improved. With heating the releasing of the sample in the second step is improved.

The sample matrix is removed with the device according to the present invention while the sample is retained in the active material. The selection of the active material depends on the composition of the sample and the substances for analytical investigation. In a particularly advantageous way the device enables focusing the volatile and substances with high boiling points: substances with high boiling points are adsorbed or retained in the active material after a small passage length already. Volatile substances deeply enter into the active material. The release, however, is effected in the opposite direction whereby volatile substances and substances with high boiling points will simultaneously arrive at the column connection.

Preferably, a cooling trap is provided downstream of the column. The control means may also comprise an auxiliary gas connection downstream of the column adapted to generate a gas pressure inside the column which is sufficient to avoid carrier gas entering in the first setting. The auxiliary gas connection may be installed upstream or downstream to the cooling trap. By setting a higher pressure in the column than in the liner, an early entering of the sample into the column is avoided. If the sample is evaporated and the carrier gas flow is reversed, the pressure in the column is lowered. Thereby the sample is flowed through the column. In such a way expensive valve constructions are avoided.

In a similar way the control means may comprise pressure controlling means for controlling the pressure at the carrier gas connection. If the pressure on the liner is controlled, with pressure no carrier gas will enter or be removed. By increasing the pressure, the carrier gas is flowed into the space between the liner and the outer tube.

The device may comprise a shut-off valve in the split outlet. It can be used in the second setting to close the split outlet if the carrier gas flow flows from the carrier gas supply in the outer tube to the column connection.

The device can be designed in such a way, that the sample reservoir comprises a receiving device for automated reception of samples or sample containers and transfer means for transferring sample vapor into the liner. The means for transferring can be formed by, for example, a heated transfer line in the liner.

A method according to the present invention is characterized in that the sample vapour is generated by heating a sample reservoir which is present in the same container as the active material.

Preferably, when generating a carrier gas flow through the active material in the opposite direction in order to include the sample contained in the active material into the carrier gas flow the active material is heated. A suitable heating coil can be provided around the outer tube in the range of the active material.

In a further modification of the invention, when flowing the sample vapor carrier gas flow through an active material selected in such a way that the sample remains in the active material and the remaining carrier gas flow passes through the active material the active material is cooled. For this purpose, a cooling medium can be flowed into the range of the active material, for example into the spaces between the heating coil.

The sample vapor is generated by heating a sample reservoir which is contained in the same container as the active material. The sample reservoir and the active material may be contained in a liner having a first heating coil in the range of the sample reservoir and a second heating coil in the range of the active material. The sample reservoir can be formed by a small sampling tube which is coaxially held in the upper portion of the liner. Sample vapor generated during the heating step will then fill the liner.

In an alternative modification of the invention, the sample vapor is generated by heating a sample reservoir outside the container containing the active material. The sample reservoir is then not limited with its outer diameters. In particular, large sample reservoirs and autosamplers may be used.

Further modifications of the present invention are subject matter of the subclaims. Embodiments are described below in greater detail with reference to the accompanying drawings.

DESCRIPTION OF THE EMBODIMENTS

Figure 1:
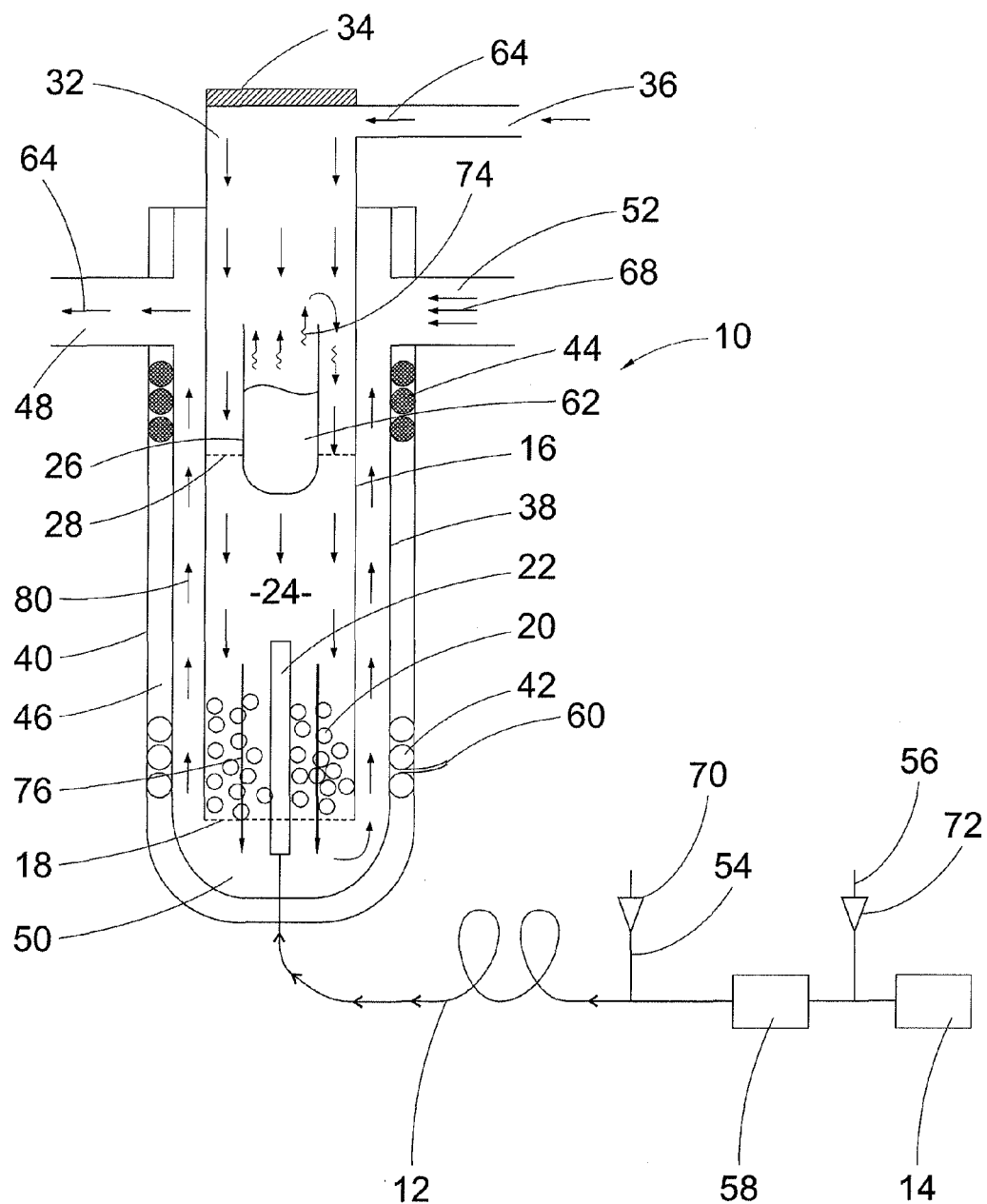
FIG. 1 is a schematic cross section through a sample preparation device in a first setting.

FIG. 1 shows a device for the preparation of a sample for gas chromatography, generally denoted with numeral 10. The device is connected upstream to a column 12. A suitable detector 14 is connected to the column 12. Columns 12 and detectors 14 are well known in the art of gas chromatography and need not be described here in greater detail.

The device 10 comprises a tubular liner 16 made of glass and having an inner diameter of some mm. The liner 16 is provided with a permeable bottom 18. Adsorbing material 20 is held on the bottom 18. The selection of the adsorbing material 20 depends on the analytic task.

The end 22 of the column 12 extends through the bottom 18 and through the adsorbing material 20 into the inside of liner 16.

A sample reservoir 26 is held in the upper portion of the liner. A permeable, inert holding device 28 is provided for this purpose. It is understood that any kind of holding device is suitable. In the present embodiment, the holding device comprises permanent magnets holding a steel ring at the sample reservoir 26.

A sample 62 is present in the sample reservoir 26 for separation and/or investigation by means of gas chromatography. The sample is treated or not treated and may comprise solid materials or residues with a high boiling point.

The liner 16 is closed with a plug 34 at its upper end 32. Furthermore, a carrier gas connection 36 is provided in the upper portion. Nobel gas, nitrogen or hydrogen or any other suitable carrier gases or mixtures of carrier gasses are provided from a controllable carrier gas supply (not shown).

The liner 16 is coaxially placed in an outer tube 38. The outer tube 38 is placed in a sleeve 40. Two heating coils 42 and 44 are provided between this double-wall tubular construction. the heating coils are connected to a current- or voltage source and controlled by a controller. The heating coil 42 is around the active material 20 in the lower range. The heating coil 44 is wound around the sample reservoir in the upper range. For evaporation of the sample the sample reservoir 26 is heated. For heating the active material a heating current is generated in the heating coil 42. Thereby, the range of the active material 20 is heated.

A space 46 is formed between the outer tube 38 and the liner 16. The space 46 is essentially an annular space connected through channels or holes in the bottom range 50 to the inside of the liner 16. A split outlet 48 is provided in the upper range of the outer tube 38. Furthermore, a carrier gas connection 52 is provided in the upper range of the outer tube for supplying carrier gas to the space.

A further carrier gas connection 54 is provided downstream of the column 12. A further carrier gas connection 56 is provided downstream of a cooling trap 58 downstream of the column. Cooling medium can be flowed from a cooling medium supply 60 into the spaces between the heating coil 42. In such a way the active material 20 can be cooled.

The described device operates as follows:
First, a sample 62 is entered into the sample reservoir 26. The sample reservoir 26 is introduced from above into the open liner 16 into the holding device 28. Then, the liner 16 is plugged. The device 10 is then set up in a first setting, which is shown in FIG. 1. In this setting, carrier gas is flowed from connection 36 into the liner 16. This is represented by arrows 64.

Simultaneously, the sample reservoir 26 with the sample 62 is heated by means of the heating coil 44. The switched-on heating coil 44 is represented by filled cross sections. The heating coil 42 is cold. This is represented by empty cross sections. Instead, cooling medium is flowed from a connection 60 into the spaces between the heating coil 42. In such a way the active material 20 is cooled.

The split outlet 48 is open. This is represented by an arrow 64. A carrier gas pressure is applied to the connections 52, 54 and 56 which is in the range of the gas pressure inside the liner 16 or slightly above. This is represented by arrows 68, 70 and 72. In such a way early entering of gases is avoided. The sample 62 is heated and then slowly evaporated into the inside 24 of the liner 16. This is represented by arrows 74. The evaporated sample 74 flows through the active material 20 together with carrier gas 64 from the supply 36. The carrier gas 64 flows through the active material 20 without resistance. This is represented by arrows 76. The sample 74 is adsorbed by the active material 20 and retained. Low-volatile sample components with high boiling points early remain in the upper range of the active material 20. High-volatile components of the sample with low boiling points enter deeply into the active material 20 and are retained in the lower range of the active material 20. It is understood, that sufficient active material 20 is used and that the density of the active material is selected in such a way, that all desired sample components are retained therein.

Figure 2:
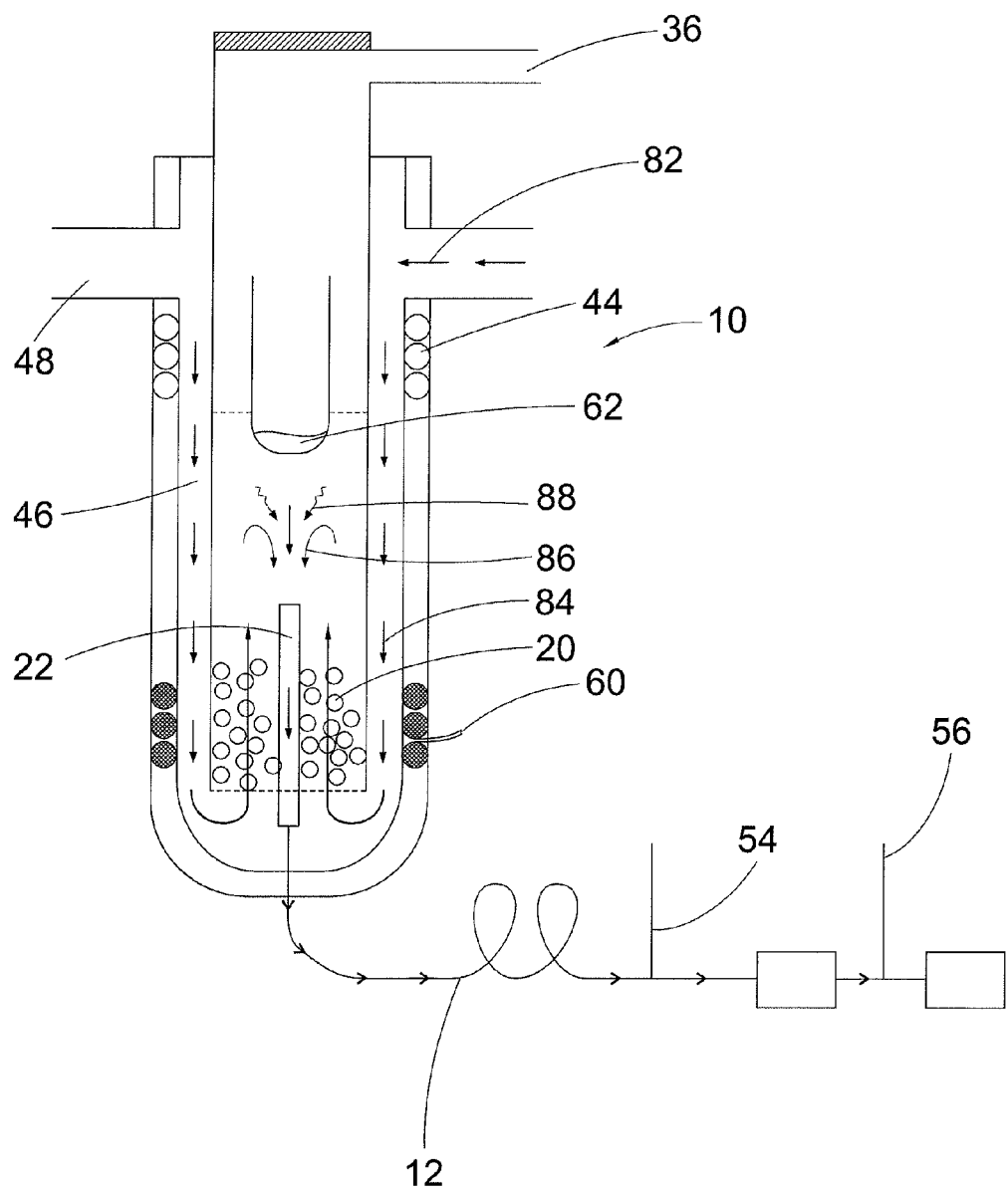
FIG. 2 shows the sample preparation device of FIG. 1 in a second setting.

The carrier gas flows upwards in the space 46. This is represented by arrows 80. The carrier gas is removed through the split outlet 48. The first setting, which is shown in FIG. 1, is maintained until the sample 62 is evaporated in the desired amount. This provides the possibility that unwanted residues of the matrix, such as solids or sample components with a high boiling point remain in the sample reservoir 26 (see FIG. 2). After the evaporation of the desired amount, the device is switched to a second setting. This is shown in FIG. 2.

In the second setting no carrier gas is supplied through connection 36. The split outlet 48 is closed. The heating 44 is switched off. The cooling supply 60 is switched off. The carrier gas pressure at the connections 54 and 56 is switched off. Simultaneously or afterwards, the active material 20 is heated with the heating coil 42. Carrier gas is flowed from the connection 52 to the space 46. This is represented by arrows 82 and 84. It can be seen that in the second setting, the carrier gas flow 84 runs in the opposite direction from top to bottom in the space 46 as in the first setting in FIG. 1.

The carrier gas is flowed through the heated active material 20, also in the opposite direction from the bottom to the top. The sample retained therein is evaporated by the heat. The carrier gas flow absorbs the sample. The carrier gas represented by arrows 86 and the sample represented by arrows 88 flow through the column connection 22 into the column 12. There, the sample is separated and analyzed in a known manner.

The described device has the advantage that the sample can be slowly evaporated. It need not be extensively prepared and thereby enables online analysis of processes. With this method, low-volatile and high-volatile components of the sample are separated from the matrix and are simultaneously present in the liner. This good focusing enables particularly sharp peaks during separation in the column even with slow evaporation. A flash-evaporation is not necessary.

Depending on the switching state of the carrier gas connections 54 and 56, the column 12 and/or the cooling trap 58 can be flushed back with carrier gas. Instead of carrier gas, any other auxiliary gas may be used for this purpose. The gas applied at the connections serves to switch the column on and off and for flushing back.

A further, alternative embodiment of the invention (not shown) operates with a thermodesorption tube. No liquid sample is evaporated with this method, but a gaseous sample is flowed through the tube. There, the sample components which shall be analyzed are adsorbed. The remaining gas is removed. By flushing back the tube with a carrier gas the accumulated sample is re-desorbed and can be fed to a suitable analytic instrument, such as a gas chromatograph. The tube is independent of the analytic instrument and is coupled in reversed position to the analytic instrument after the adsorption process.

The foregoing detailed description describes the invention with reference to specific representative embodiments. However, it will be appreciated that various modifications and changes can be made without departing from the scope of the present invention as set forth in the appended claims. The detailed description and accompanying drawings are to be regarded as illustrative, rather than restrictive, and any such modifications or changes are intended to fall within the scope of the present invention as described and set forth herein.

What is claimed is:

1. A Device for the preparation of samples for gas chromatography, comprising
    a carrier gas supply
    a tubular liner adapted to be flushed with carrier gas from said carrier gas supply, and having an inside, a lower and an upper end portion;
    a controllably heated sample reservoir;
    an active material provided in said tubular liner;
    an outer tube coaxially arranged around said liner, whereby a space is formed between said liner and said outer tube, said space being in contact with said lower end portion of the liner;
    a split outlet provided at said outer tube;
    a carrier gas connection provided at said outer tube for feeding carrier gas into said space;
    a column connection above said active material for connecting a gas chromatographic column; and
    control means for controlling a flow of said carrier gas
        in a first setting from said inside of said liner through said active material, and
        in a second setting from said carrier gas connection in the opposite direction through said active material to said column connection;
    and wherein
    said lower end portion of said liner is adapted to be controllably heated;
    said sample reservoir is placed inside said liner or is adapted to be inserted into said liner together with a sample;
    said active material is provided in said controllably heated, lower end portion of said liner;
    said column connection for connecting a gas chromatographic column is provided above said active material;
    said flow of said carrier gas is flowed in the first setting from said active material into said space and from there to said split outlet; and
    said flow of said carrier gas in the second setting flows in the opposite direction through said space and afterwards through said active material.

2. The device of claim 1, wherein said sample reservoir is present in said upper end portion of said liner.

3. The device of claim 2, wherein said sample reservoir is magnetically mounted in said upper end portion of said liner.

4. The device of claim 1, wherein said active material is an adsorbent or a phase material.

5. The device of claim 1, wherein said active material can be heated and/or cooled.

6. The device of claim 1, wherein a cooling trap is provided downstream said column.

7. The device of claim 1, wherein said control means comprise an auxiliary gas connection downstream said column adapted to generate a gas pressure inside said column which is sufficient to avoid carrier gas entering in said first setting.

8. The device of claim 1, wherein said control means comprise pressure controlling means for controlling the pressure at said carrier gas connection.

9. The device of claim 1, wherein a shut-off valve is provided in said split outlet.

10. The device of claim 1, wherein said sample reservoir comprises a receiving device for automated reception of samples or sample containers and transfer means for transferring sample vapor into said liner.

11. Method for the preparation of samples for analytic purposes, comprising the steps of:
    generating a gas flow comprising a gaseous sample by evaporation of a sample and generating a carrier gas flow containing the sample vapor;
    flowing the carrier gas flow comprising the sample vapor through an active material comprised in a container placed in an outer tube the active material selected in such a way that the sample remains in the active material and the remaining gas flow passes through the active material;
    removing the carrier gas flow passed through the active material through a space formed between the container and the outer tube and through a split outlet towards the outside;
    generating a carrier gas flow through the active material in the opposite direction in order to include the sample contained in the active material into the carrier gas flow; and
    flowing the sample-carrier gas flow to a gas chromatography column,
    and wherein
    the sample vapor is generated by heating a sample reservoir which is present in the same container as the active material.

12. The method of claim 11, wherein the active material is heated during the step of generating a carrier gas flow through the active material in the opposite direction.

13. The method of claim 11, wherein the active material is cooled during the step of flowing the carrier gas flow comprising the sample vapor through an active material.

* * * * *